United States Patent [19]

Payne et al.

[11] Patent Number: 5,632,987
[45] Date of Patent: May 27, 1997

[54] BACILLUS THURINGIENSIS TOXINS ACTIVE AGAINST CORN ROOTWORM LARVAE

[75] Inventors: Jewel Payne, Davis; Kenneth E. Narva, San Diego, both of Calif.

[73] Assignee: Mycogen Corporation, San Diego, Calif.

[21] Appl. No.: 357,698

[22] Filed: Dec. 16, 1994

Related U.S. Application Data

[60] Division of Ser. No. 176,403, Dec. 30, 1993, abandoned, which is a continuation-in-part of Ser. No. 999,053, Dec. 31, 1992, abandoned.

[51] Int. Cl.$^6$ ................................................ A01N 63/00
[52] U.S. Cl. .................................. 424/93.461; 435/252.1; 514/12
[58] Field of Search ..................... 424/93 A, 93 L, 424/93.461; 435/252.3, 252.31, 252.5, 252.1; 514/12

[56] References Cited

U.S. PATENT DOCUMENTS

| | | | |
|---|---|---|---|
| 4,448,885 | 5/1984 | Schnepf et al. | 435/172.3 |
| 4,467,036 | 8/1984 | Schnepf et al. | 435/69.1 |
| 4,797,276 | 1/1989 | Herrnstadt et al. | 424/93 L |
| 4,849,217 | 7/1989 | Soares et al. | 424/93 L |
| 4,853,331 | 8/1989 | Herrnstadt et al. | 435/252.1 |
| 4,918,006 | 4/1990 | Ellar et al. | 435/69.1 |
| 4,948,734 | 8/1990 | Edwards et al. | 435/252.5 |
| 5,151,363 | 9/1992 | Payne | 435/252.5 |
| 5,187,091 | 2/1993 | Donovan et al. | 435/240.4 |
| 5,208,077 | 5/1993 | Proctor et al. | 427/461 |

OTHER PUBLICATIONS

Gaertner, F.H., L. Kim (1988) "Current Applied Recombinant DNA Projects" TIBTECH 6:S4–S7.

Gaertner, F.H. (1989) "Cellular delivery systems for insecticidal proteins: living a non–living microorganisms" Controlled Deliver of Crop–Protection Agents 245–255.

Couch, T.L. (1980) "Mosquito Pathogenicity of *Bacillus thuringiensis* var. *israelensis*" Developments in Industrial Microbiology 22:61–76.

Beegle, C.C. (1978) "Use of Entomogenous Bacteria in Agroecosystems" Developments in Industrial Microbiology 20:97–104.

Krieg, A., et al. (1983) "*Bacillus thuringiensis* var. *tenebrionis*: ein neuer gegenuber Larven von Coleopteren wirksamer Pathotyp" Z. ang. Ent. 96:500–508.

Hofte, H., H.R. Whiteley (1989) "Insecticidal Crystal Proteins of *Bacillus thuringiensis*" Microbiological Reviews 52(2):242–255.

Feitelson, J.S., et al. (1992) "*Bacillus thuringiensis*: Insects and Beyond" Bio/Technology 10:271–275.

Schnepf, H.E., et al. (1981) "Cloning and expression of the *Bacillus thuringiensis* crystal protein gene in *Escherichia coli*" Proc. Natl. Acad. Sci. USA 78:2893–2897.

Murray, E.E. et al. (1991) "Analysis of unstable RNA transcripts of insecticidal crystal protein genes of *Bacillus thuringiensis* in transgenic plants and electroporated protoplasts" Plant Molecular Biology 16:1035 (abstract).

Perlak, F.J. et al. (1991) "Modification of the coding sequence enhances plant expressin of insect control protein genes" Proc. Natl. Acad. Sci. USA 88:3324 (abstract).

*Primary Examiner*—Che S. Chereskin
*Attorney, Agent, or Firm*—Saliwanchik, Lloyd & Saliwanchik

[57] ABSTRACT

Disclosed and claimed are toxins and genes from *Bacillus thuringiensis* strains designated PS80JJ1, PS158D5, PS167P, PS169E, PS177F1, PS177G, PS204G4, PS204G6 which can be used to control corn rootworm. Mutants which retain the activity of the parent strain can be used to control the pest. Further, isolated spores or purified toxins from these isolates can be used to control corn rootworm. Genes encoding δ-endotoxins can be removed from these strains using standard well-known techniques, and transferred to other hosts. Expression of the δ-endotoxin in such hosts results in control of corn rootworm larvae.

11 Claims, No Drawings

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Gly  Asn  Phe  Asn  Xaa  Glu  Lys  Asp  Tyr  Asp
                          5                             10

( 2 ) INFORMATION FOR SEQ ID NO:2:

( i ) SEQUENCE CHARACTERISTICS:
           ( A ) LENGTH: 41 bases
           ( B ) TYPE: nucleic acid
           ( C ) STRANDEDNESS: single
           ( D ) TOPOLOGY: linear ( i i ) MOLECULE TYPE: DNA (synthetic)

( x i ) SEQUENCE DESCRIPTION: SEQ ID NO:2:

AGACGTGGAT  CCGGAAATTT  TAATTTGAA  AARGA Y TA Y G A              41

( 2 ) INFORMATION FOR SEQ ID NO:3:

( i ) SEQUENCE CHARACTERISTICS:
           ( A ) LENGTH: 23 bases
           ( B ) TYPE: nucleic acid
           ( C ) STRANDEDNESS: single
           ( D ) TOPOLOGY: linear ( i i ) MOLECULE TYPE: DNA (synthetic)

( x i ) SEQUENCE DESCRIPTION: SEQ ID NO:3:

GGACCAGGAT  TTACAGGWGG  RRA                                              23

( 2 ) INFORMATION FOR SEQ ID NO:4:

( i ) SEQUENCE CHARACTERISTICS:
           ( A ) LENGTH: 29 bases
           ( B ) TYPE: nucleic acid
           ( C ) STRANDEDNESS: single
           ( D ) TOPOLOGY: linear ( i i ) MOLECULE TYPE: DNA (synthetic)

( x i ) SEQUENCE DESCRIPTION: SEQ ID NO:4:

TAACGTGTAT  WCGSTTTTAA  TTTWGA Y TC                            29

( 2 ) INFORMATION FOR SEQ ID NO:5:

( i ) SEQUENCE CHARACTERISTICS:
           ( A ) LENGTH: 3561 base pairs
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:5:

| | | | | | |
|---|---|---|---|---|---|
| ATGGATTGTA | ATTTACAATC | ACAACAAAAT | ATTCCTTATA | ATGTATTAGC | AATACCAGTA | 60 |
| TCTAATGTTA | ATGCGTTGGT | TGATACAGCT | GGAGATTTAA | AAAAGCATG | GAAGAATTT | 120 |
| CAAAAAACTG | GTTCTTTTTC | ATTAACAGCT | TTACAACAAG | GATTTCTGC | CTCACAAGGA | 180 |
| GGAGCATTCA | ATTATTTAAC | ATTATTACAA | TCAGGAATAT | CATTAGCTGG | TTCTTTTGTC | 240 |
| CCTGGAGGTA | CTTTTGTAGC | ACCCATTGTT | AATATGGTTA | TTGGTTGGTT | ATGGCCACAT | 300 |
| AAAACAAGA | CAGCGGATAC | AGAAAATTTA | ATAAAATTAA | TTGATGAAGA | AATTCAAAAA | 360 |
| CAATTAAACA | AAGCCTTATT | AGACCAAGAT | AGAAACAATT | GGACCTCTTT | TTTAGAAAGT | 420 |
| ATATTTGATA | CTTCAGCTAC | AGTAAGTAAT | GCAATTATAG | ATGCACAGTG | GTCAGGTACT | 480 |

| | | | | | | |
|---|---|---|---|---|---|---|
| GTAGATACTA | CAAATAGACA | ACAAAAAACT | CCAACAACAT | CAGATTATCT | AAATGTTGTT | 540 |
| GGAAAATTTG | ATTCAGCGGA | TTCTTCAATT | ATAACTAATG | AAAATCAAAT | AATGAATGGC | 600 |
| AACTTTGACG | TAGCTGCAGC | ACCCTATTTT | GTTATAGGAG | CAACATTACG | TCTTTCATTA | 660 |
| TATCAATCTT | ATATTAAATT | TTGTAATAGT | TGGATTGATG | CAGTTGGATT | TAGTACAAAT | 720 |
| GATGCTAATA | CACAAAAAGC | TAATTTAGCT | CGTACGAAAT | TAACTATGCG | TACTACAATT | 780 |
| AATGAATATA | CACAAAGAGT | TATGAAAGTT | TTTAAAGATT | CCAAGAATAT | GCCTACAATA | 840 |
| GGTACTAATA | AATTTAGTGT | TGATGCTTAT | AATGTATATG | TTAAAGGAAT | GACATTAAAT | 900 |
| GTTTTAGATA | TGGTAGCAAT | ATGGTCTTCA | TTATATCCAA | ATGATTATAC | TTCACAAACA | 960 |
| GCCATAGAAC | AAACACGTGT | CACTTTTTCA | AATATGGTTG | GACAAGAAGA | AGGTACAGAT | 1020 |
| GGAACCCTAA | AAATTTACAA | TACTTTTGAT | TCTCTTAGTT | ATCAACATAG | CCTAATACCT | 1080 |
| AATAATAATG | TTAATTTAAT | TTCTTATTAT | ACTGATGAAT | TGCAAAATCT | AGAATTAGCA | 1140 |
| GTATATACTC | CTAAAGGTGG | AAGTGGATAC | GCTTATCCTT | ATGGATTTAT | TTTAAATTAT | 1200 |
| GCAAACAGCA | ACTACAAATA | TGGTGATAAT | GATCCAACAG | GCAAACCATT | AAATAAACAA | 1260 |
| GATGGACCTA | TACAACAAAT | AAATGCAGCA | ACTCAAAACA | GTAAATATCT | AGATGGAGAA | 1320 |
| ACAATAAATG | GAATAGGGGC | ATCCTTACCT | GGTTATTGTA | CTACAGGATG | TTCAGCAACA | 1380 |
| GAACAACCTT | TTAGTTGTAC | TTCTACTGCT | AATAGCTATA | AGCAAGCTG | TAATCCTTCA | 1440 |
| GATACTAATC | AAAAAATTAA | TGCTTTATAT | GCTTTACAC | AAACTAATGT | AAAGGGAAGC | 1500 |
| ACGGGGAAAT | TAGGAGTACT | GGCAAGTCTT | GTTCCATATG | ATTTAAATCC | TAAAAATGTA | 1560 |
| TTTGGTGAAT | TAGATTCAGA | TACAAATAAT | GTTATCTTAA | AAGGAATTCC | TGCAGAAAAA | 1620 |
| GGGTATTTTC | CTAATAATGC | GCGACCTACT | GTTGTAAAAG | AATGGATTAA | TGGTGCAAGT | 1680 |
| GCTGTACCAT | TTATTCAGG | AAATACTTTA | TTTATGACGG | CTACGAATTT | AACAGCTACT | 1740 |
| CAATATAAAA | TTAGAATACG | TTATGCAAAT | CCAAATTCAG | ATACTCAAAT | CGGTGTACTA | 1800 |
| ATTACGCAAA | ATGGTTCTCA | AATTTCCAAT | AGTAATCTAA | CACTTTATAG | TACTACTGAT | 1860 |
| TCAAGTATGA | GTAGTAATTT | ACCACAAAAT | GTATATGTCA | CAGGGGAAAA | TGGAAATTAT | 1920 |
| ACACTTCTAG | ATTTATATAG | TACTACTAAT | GTTTATCAA | CAGGAGATAT | TACATTAAAA | 1980 |
| CTTACAGGAG | GAAATCAAAA | AATATTTATT | GATCGAATAG | AATTTATTCC | TACTATGCCT | 2040 |
| GTACCTGCTC | CTACTAATAA | CACTAATAAC | AATAACGGCG | ATAACGGCAA | TAACAATCCC | 2100 |
| CCACACCACG | GTTGTGCAAT | AGCTGGTACA | CAACAACTTT | GTTCTGGACC | ACCTAAGTTT | 2160 |
| GAACAAGTAA | GTGATTTAGA | AAAAATTACA | ACGCAAGTAT | ATATGTTATT | CAAATCTTCT | 2220 |
| TCGTATGAAG | AATTAGCTCT | AAAAGTTTCT | AGCTATCAAA | TTAATCAAGT | GGCATTGAAA | 2280 |
| GTTATGGCAC | TATCTGATGA | AAAGTTTTGT | GAAGAAAAA | GATTGTTACG | AAAATTAGTC | 2340 |
| AATAAAGCAA | ACCAATTACT | AGAAGCACGT | AACTTACTAG | TAGGTGGAAA | TTTTGAAACA | 2400 |
| ACTCAAAATT | GGGTACTTGG | AACAAATGCT | TATATAAATT | ATGATTCGTT | TTTATTTAAT | 2460 |
| GGAAATTATT | TATCCTTACA | ACCAGCAAGT | GGATTTTTCA | CATCTTATGC | TTATCAAAAA | 2520 |
| ATAGATGAGT | CAACATTAAA | ACCATATACA | CGATATAAAG | TTTCTGGATT | CATTGGGCAA | 2580 |
| AGTAATCAAG | TAGAACTTAT | TATTTCTCGT | TATGGAAAAG | AAATTGATAA | AATATTAAAT | 2640 |
| GTTCCATATG | CAGGGCCTCT | TCCTATTACT | GCTGATGCAT | CGATAACTTG | TTGTGCACCA | 2700 |
| GAAATAGACC | AATGTGATGG | GGGGCAATCT | GATTCTCATT | TCTTCAACTA | TAGCATCGAT | 2760 |
| GTAGGTGCAC | TTCACCCAGA | ATTAAACCCT | GGCATTGAAA | TTGGTCTTAA | AATTGTGCAA | 2820 |
| TCAAATGGTT | ATATAACAAT | TAGTAATCTA | GAAATTATTG | AAGAACGTCC | ACTTACAGAA | 2880 |

-continued

```
ATGGAAATTC AAGCAGTCAA TCGAAAAGAT CACAAATGGA AAAGAGAAAA ACTTCTAGAA        2940

TGTGCAAGTG TTAGTGAACT TTTACAACCA ATCATTAATC AAATCGATTC ATTGTTCAAA        3000

GATGCAAACT GGTATAATGA TATTCTTCCT CATGTCACAT ATCAAACTCT AAAAAATATT        3060

ATAGTACCCG ATTTACCAAA ATTAAACAT  TGGTTCATAG ATCATCTCCC AGGTGAATAT        3120

CATGAAATTG AACAACAAAT GAAAGAAGCT CTAAAACATG CATTTACACA ATTAGACGAG        3180

AAAAATTTAA TCCACAATGG TCACTTTGCA ACTAACTTAA TAGATTGGCA AGTAGAAGGT        3240

GATGCTCGAA TGAAAGTATT AGAAAATAAT GCTTGGCAT  ACAACTTTC  CAATTGGGAT        3300

TCTAGTGTTT CACAATCTAT TGATATATTA GAATTTGATG AAGATAAAGC ATATAAACTT        3360

CGCGTATATG CTCAAGGAAG CGGAACAATC CAATTTGGAA ACTGTGAAGA TGAAGCCATC        3420

CAATTTAATA CAAACTCATT CGTATATAAA GAAAAAATAA TCTATTTCGA TACCCCATCA        3480

ATTAACTTAC ACATACAATC AGAAGGTTCT GAATTCGTTG TAAGTAGTAT CGACCTCGTT        3540

GAATTATCAG ACGACGAATA A                                                  3561
```

( 2 ) INFORMATION FOR SEQ ID NO:6:

( i ) SEQUENCE CHARACTERISTICS:
        ( A ) LENGTH: 1186 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Met Asp Cys Asn Leu Gln Ser Gln Gln Asn Ile Pro Tyr Asn Val Leu
 1               5                  10                  15

Ala Ile Pro Val Ser Asn Val Asn Ala Leu Val Asp Thr Ala Gly Asp
            20                  25                  30

Leu Lys Lys Ala Trp Glu Glu Phe Gln Lys Thr Gly Ser Phe Ser Leu
        35                  40                  45

Thr Ala Leu Gln Gln Gly Phe Ser Ala Ser Gln Gly Gly Ala Phe Asn
    50                  55                  60

Tyr Leu Thr Leu Leu Gln Ser Gly Ile Ser Leu Ala Gly Ser Phe Val
 65                  70                  75                  80

Pro Gly Gly Thr Phe Val Ala Pro Ile Val Asn Met Val Ile Gly Trp
                85                  90                  95

Leu Trp Pro His Lys Asn Lys Thr Ala Asp Thr Glu Asn Leu Ile Lys
            100                 105                 110

Leu Ile Asp Glu Glu Ile Gln Lys Gln Leu Asn Lys Ala Leu Leu Asp
        115                 120                 125

Gln Asp Arg Asn Asn Trp Thr Ser Phe Leu Glu Ser Ile Phe Asp Thr
    130                 135                 140

Ser Ala Thr Val Ser Asn Ala Ile Ile Asp Ala Gln Trp Ser Gly Thr
145                 150                 155                 160

Val Asp Thr Thr Asn Arg Gln Gln Lys Thr Pro Thr Thr Ser Asp Tyr
                165                 170                 175

Leu Asn Val Val Gly Lys Phe Asp Ser Ala Asp Ser Ser Ile Ile Thr
            180                 185                 190

Asn Glu Asn Gln Ile Met Asn Gly Asn Phe Asp Val Ala Ala Ala Pro
        195                 200                 205

Tyr Phe Val Ile Gly Ala Thr Leu Arg Leu Ser Leu Tyr Gln Ser Tyr
    210                 215                 220

Ile Lys Phe Cys Asn Ser Trp Ile Asp Ala Val Gly Phe Ser Thr Asn
```

-continued

|     |     |     | 225 |     |     |     |     | 230 |     |     |     |     | 235 |     |     |     |     | 240 |     |
| --- | --- | --- | --- | --- | --- | --- | --- | --- | --- | --- | --- | --- | --- | --- | --- | --- | --- | --- | --- |

Asp Ala Asn Thr Gln Lys Ala Asn Leu Ala Arg Thr Lys Leu Thr Met
            245                    250               255

Arg Thr Thr Ile Asn Glu Tyr Thr Gln Arg Val Met Lys Val Phe Lys
            260                   265              270

Asp Ser Lys Asn Met Pro Thr Ile Gly Thr Asn Lys Phe Ser Val Asp
      275                280               285

Ala Tyr Asn Val Tyr Val Lys Gly Met Thr Leu Asn Val Leu Asp Met
   290                   295            300

Val Ala Ile Trp Ser Ser Leu Tyr Pro Asn Asp Tyr Thr Ser Gln Thr
305               310               315            320

Ala Ile Glu Gln Thr Arg Val Thr Phe Ser Asn Met Val Gly Gln Glu
            325                   330            335

Glu Gly Thr Asp Gly Thr Leu Lys Ile Tyr Asn Thr Phe Asp Ser Leu
          340                 345            350

Ser Tyr Gln His Ser Leu Ile Pro Asn Asn Asn Val Asn Leu Ile Ser
        355              360              365

Tyr Tyr Thr Asp Glu Leu Gln Asn Leu Glu Leu Ala Val Tyr Thr Pro
   370                 375              380

Lys Gly Gly Ser Gly Tyr Ala Tyr Pro Tyr Gly Phe Ile Leu Asn Tyr
385               390              395            400

Ala Asn Ser Asn Tyr Lys Tyr Gly Asp Asn Asp Pro Thr Gly Lys Pro
            405               410            415

Leu Asn Lys Gln Asp Gly Pro Ile Gln Gln Ile Asn Ala Ala Thr Gln
            420               425            430

Asn Ser Lys Tyr Leu Asp Gly Glu Thr Ile Asn Gly Ile Gly Ala Ser
      435              440            445

Leu Pro Gly Tyr Cys Thr Thr Gly Cys Ser Ala Thr Glu Gln Pro Phe
450               455              460

Ser Cys Thr Ser Thr Ala Asn Ser Tyr Lys Ala Ser Cys Asn Pro Ser
465               470              475            480

Asp Thr Asn Gln Lys Ile Asn Ala Leu Tyr Ala Phe Thr Gln Thr Asn
            485               490            495

Val Lys Gly Ser Thr Gly Lys Leu Gly Val Leu Ala Ser Leu Val Pro
          500               505            510

Tyr Asp Leu Asn Pro Lys Asn Val Phe Gly Glu Leu Asp Ser Asp Thr
      515              520              525

Asn Asn Val Ile Leu Lys Gly Ile Pro Ala Glu Lys Gly Tyr Phe Pro
   530                 535            540

Asn Asn Ala Arg Pro Thr Val Val Lys Glu Trp Ile Asn Gly Ala Ser
545               550              555            560

Ala Val Pro Phe Tyr Ser Gly Asn Thr Leu Phe Met Thr Ala Thr Asn
          565             570            575

Leu Thr Ala Thr Gln Tyr Lys Ile Arg Ile Arg Tyr Ala Asn Pro Asn
        580              585              590

Ser Asp Thr Gln Ile Gly Val Leu Ile Thr Gln Asn Gly Ser Gln Ile
      595              600              605

Ser Asn Ser Asn Leu Thr Leu Tyr Ser Thr Thr Asp Ser Ser Met Ser
   610                615              620

Ser Asn Leu Pro Gln Asn Val Tyr Val Thr Gly Glu Asn Gly Asn Tyr
625               630              635            640

Thr Leu Leu Asp Leu Tyr Ser Thr Thr Asn Val Leu Ser Thr Gly Asp
          645             650            655

-continued

| | | | | | | | | | | | | | | |
|---|---|---|---|---|---|---|---|---|---|---|---|---|---|---|
| Ile | Thr | Leu | Lys<br>660 | Leu | Thr | Gly | Gly<br>665 | Asn | Gln | Lys | Ile<br>670 | Phe | Ile | Asp | Arg |
| Ile | Glu | Phe<br>675 | Ile | Pro | Thr | Met | Pro<br>680 | Val | Pro | Ala | Pro<br>685 | Thr | Asn | Asn | Thr |
| Asn | Asn<br>690 | Asn | Asn | Gly | Asp | Asn<br>695 | Gly | Asn | Asn | Asn | Pro<br>700 | Pro | His | His | Gly |
| Cys<br>705 | Ala | Ile | Ala | Gly | Thr<br>710 | Gln | Gln | Leu | Cys | Ser<br>715 | Gly | Pro | Pro | Lys | Phe<br>720 |
| Glu | Gln | Val | Ser | Asp<br>725 | Leu | Glu | Lys | Ile | Thr<br>730 | Thr | Gln | Val | Tyr | Met<br>735 | Leu |
| Phe | Lys | Ser | Ser<br>740 | Ser | Tyr | Glu | Glu<br>745 | Leu | Ala | Leu | Lys<br>750 | Val | Ser | Ser | Tyr |
| Gln | Ile | Asn<br>755 | Gln | Val | Ala | Leu | Lys<br>760 | Val | Met | Ala | Leu<br>765 | Ser | Asp | Glu | Lys |
| Phe | Cys<br>770 | Glu | Glu | Lys | Arg<br>775 | Leu | Leu | Arg | Lys<br>780 | Leu | Val | Asn | Lys | Ala | Asn |
| Gln<br>785 | Leu | Leu | Glu | Ala | Arg<br>790 | Asn | Leu | Leu | Val<br>795 | Gly | Gly | Asn | Phe | Glu | Thr<br>800 |
| Thr | Gln | Asn | Trp | Val<br>805 | Leu | Gly | Thr | Asn<br>810 | Ala | Tyr | Ile | Asn | Tyr<br>815 | Asp | Ser |
| Phe | Leu | Phe | Asn<br>820 | Gly | Asn | Tyr | Leu | Ser<br>825 | Leu | Gln | Pro | Ala | Ser<br>830 | Gly | Phe |
| Phe | Thr | Ser<br>835 | Tyr | Ala | Tyr | Gln | Lys<br>840 | Ile | Asp | Glu | Ser | Thr<br>845 | Leu | Lys | Pro |
| Tyr | Thr<br>850 | Arg | Tyr | Lys | Val | Ser<br>855 | Gly | Phe | Ile | Gly | Gln<br>860 | Ser | Asn | Gln | Val |
| Glu<br>865 | Leu | Ile | Ile | Ser | Arg<br>870 | Tyr | Gly | Lys | Glu | Ile<br>875 | Asp | Lys | Ile | Leu | Asn<br>880 |
| Val | Pro | Tyr | Ala | Gly<br>885 | Pro | Leu | Pro | Ile | Thr<br>890 | Ala | Asp | Ala | Ser | Ile<br>895 | Thr |
| Cys | Cys | Ala | Pro<br>900 | Glu | Ile | Asp | Gln | Cys<br>905 | Asp | Gly | Gly | Gln | Ser<br>910 | Asp | Ser |
| His | Phe | Phe<br>915 | Asn | Tyr | Ser | Ile | Asp<br>920 | Val | Gly | Ala | Leu | His<br>925 | Pro | Glu | Leu |
| Asn | Pro<br>930 | Gly | Ile | Glu | Ile<br>935 | Gly | Leu | Lys | Ile | Val<br>940 | Gln | Ser | Asn | Gly | Tyr |
| Ile<br>945 | Thr | Ile | Ser | Asn | Leu<br>950 | Glu | Ile | Ile | Glu | Glu<br>955 | Arg | Pro | Leu | Thr | Glu<br>960 |
| Met | Glu | Ile | Gln | Ala<br>965 | Val | Asn | Arg | Lys | Asp<br>970 | His | Lys | Trp | Lys | Arg<br>975 | Glu |
| Lys | Leu | Leu | Glu<br>980 | Cys | Ala | Ser | Val | Ser<br>985 | Glu | Leu | Leu | Gln | Pro<br>990 | Ile | Ile |
| Asn | Gln | Ile<br>995 | Asp | Ser | Leu | Phe | Lys<br>1000 | Asp | Ala | Asn | Trp | Tyr<br>1005 | Asn | Asp | Ile |
| Leu | Pro | His<br>1010 | Val | Thr | Tyr | Gln | Thr<br>1015 | Leu | Lys | Asn | Ile | Ile<br>1020 | Val | Pro | Asp |
| Leu | Pro<br>1025 | Lys | Leu | Lys | His<br>1030 | Trp | Phe | Ile | Asp | His<br>1035 | Leu | Pro | Gly | Glu | Tyr<br>1040 |
| His | Glu | Ile | Glu | Gln | Gln<br>1045 | Met | Lys | Glu | Ala | Leu<br>1050 | Lys | His | Ala | Phe<br>1055 | Thr |
| Gln | Leu | Asp | Glu | Lys<br>1060 | Asn | Leu | Ile | His | Asn<br>1065 | Gly | His | Phe | Ala | Thr<br>1070 | Asn |
| Leu | Ile | Asp | Trp<br>1075 | Gln | Val | Glu | Gly | Asp<br>1080 | Ala | Arg | Met | Lys | Val<br>1085 | Leu | Glu |

| | | | | | | | | | | | | | | |
|---|---|---|---|---|---|---|---|---|---|---|---|---|---|---|
| Asn | Asn 1090 | Ala | Leu | Ala | Leu | Gln | Leu 1095 | Ser | Asn | Trp | Asp 1100 | Ser | Ser | Val | Ser |
| Gln 1105 | Ser | Ile | Asp | Ile | Leu 1110 | Glu | Phe | Asp | Glu | Asp 1115 | Lys | Ala | Tyr | Lys | Leu 1120 |
| Arg | Val | Tyr | Ala | Gln 1125 | Gly | Ser | Gly | Thr | Ile 1130 | Gln | Phe | Gly | Asn | Cys 1135 | Glu |
| Asp | Glu | Ala | Ile 1140 | Gln | Phe | Asn | Thr | Asn 1145 | Ser | Phe | Val | Tyr | Lys 1150 | Glu | Lys |
| Ile | Ile | Tyr 1155 | Phe | Asp | Thr | Pro | Ser 1160 | Ile | Asn | Leu | His | Ile 1165 | Gln | Ser | Glu |
| Gly | Ser 1170 | Glu | Phe | Val | Val | Ser 1175 | Ser | Ile | Asp | Leu | Val 1180 | Glu | Leu | Ser | Asp |
| Asp 1185 | Glu | | | | | | | | | | | | | | |

BACILLUS THURINGIENSIS TOXINS ACTIVE AGAINST CORN ROOTWORM LARVAE

CROSS-REFERENCE TO A RELATED APPLICATION

This application is a division of application Ser. No. 08/176,403, filed Dec. 30, 1993 now abandoned; which is a continuation-in-part of application Ser. No. 07/999,053, filed on Dec. 31, 1992, now abandoned.

BACKGROUND OF THE INVENTION

The soil microbe *Bacillus thuringiensis* (B.t.) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain B.t. toxin genes have been isolated and sequenced, and recombinant DNA-based B.t. products have been produced and approved for use. In addition, with the use of genetic engineering techniques, new approaches for delivering these B.t. endotoxins to agricultural environments are under development, including the use of plants genetically engineered with endotoxin genes for insect resistance and the use of stabilized intact microbial cells as B.t. endotoxin delivery vehicles (Gaertner, F. H., L. Kim [1988] *TIBTECH* 6:S4–S7). Thus, isolated B.t. endotoxin genes are becoming commercially valuable.

Until the last ten years, commercial use of B.t. pesticides has been largely restricted to a narrow range of lepidopteran (caterpillar) pests. Preparations of the spores and crystals of *B. thuringiensis* subsp. *kurstaki* have been used for many years as commercial insecticides for lepidopteran pests. For example, *B. thuringiensis* var. *kurstaki* HD-1 produces a crystalline δ-endotoxin which is toxic to the larvae of a number of lepidopteran insects.

In recent years, however, investigators have discovered B.t. pesticides with specificities for a much broader range of pests. For example, other species of B.t., namely *israelensis* and *tenebrionis* (a.k.a.B.t. M-7, a.k.a.B.t. san diego), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255). See also Couch, T. L. (1980) "Mosquito Pathogenicity of *Bacillus thuringiensis* var. *israelensis*," *Developments in Industrial Microbiology* 22:61–76; Beegle, C. C., (1978) "*Use of Entomogenous Bacteria in Agroecosystems*," *Developments in Industrial Microbiology* 20:97–104. Krieg, A., A. M. Huger, G. A. Langenbruch, W. Schnetter (1983) Z. ang. Ent. 96:500–508, describe *Bacillus thuringiensis* var. *tenebrionis*, which is reportedly active against two beetles in the order Coleoptera. These are the Colorado potato beetle, *Leptinotarsa decemlineata*, and *Agetastica alni*.

Recently, new subspecies of B. t. have been identified, and genes responsible for active δ-endotoxin proteins have been isolated (Höfte, H., H.R. Whiteley [1989] *Microbiological Reviews* 52(2):242–255). Höfte and Whiteley classified B.t. crystal protein genes into 4 major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported. (Feitelson, J. S., J. Payne, L. Kim [1992] *Bio/Technology* 10:271–275).

The cloning and expression of a B.t. crystal protein gene in *Escherichia coli* has been described in the published literature (Schnepf, H. E., H. R. Whiteley [1981] *Proc. Natl. Acad. Sci. USA* 78:2893–2897). U.S. Pat. Nos. 4,448,885 and 4,467,036 both disclose the expression of B.t. crystal protein in *E. coli*. U.S. Pat. Nos. 4,797,276 and 4,853,331 disclose *B. thuringiensis* strain *tenebrionis* (a.k.a. M-7, a.k.a.B.t. san diego) which can be used to control coleopteran pests in various environments. U.S. Pat. No. 4,918,006 discloses B.t. toxins having activity against Dipterans. U.S. Pat. No. 4,849,217 discloses B.t. isolates which have activity against the alfalfa weevil. U.S. Pat. No. 5,208,077 discloses coleopteran-active *Bacillus thudngiensis* isolates. U.S. Pat. No. 5,151,363 and U.S. Pat. No. 4,948,734 disclose certain isolates of B.t. which have activity against nematodes. As a result of extensive research and investment of resources, other patents have issued for new B.t. isolates and new uses of B.t. isolates. However, the discovery of new B.t. isolates and new uses of known B.t. isolates remains an empirical, unpredictable art.

Approximately 9.3 million acres of U.S. corn are infested with corn rootworm species complex each year. The corn rootworm species complex includes the northern corn rootworm, *Diabrotica barberi*, the southern corn rootworm, *D. undecimpunctata howardi*, and the western corn rootworm, *D. virgifera virgifera*. The soil-dwelling larvae of these Diabrotica species feed on the root of the corn plant, causing lodging. Lodging eventually reduces corn yield and often results in death of the plant. By feeding on cornsilks, the adult beetles reduce pollination and, therefore, detrimentally effect the yield of corn per plant. In addition, adults and larvae of the genus Diabrotica attack cucurbit crops (cucumbers, melons, squash, etc.) and many vegetable and field crops in commercial production as well as those being grown in home gardens.

Control of corn rootworm has been partially addressed by cultivation methods, such as crop rotation and the application of high nitrogen levels to stimulate the growth of an adventitious root system. However, chemical insecticides are relied upon most heavily to guarantee the desired level of control. Insecticides are either banded onto or incorporated into the soil. The major problem associated with the use of chemical insecticides is the development of resistance among the treated insect populations.

BRIEF SUMMARY OF THE INVENTION

The subject invention concerns novel materials and methods for controlling corn rootworm. The materials and methods of the subject invention result from the unexpected discovery that certain B.t. isolates, as well as toxins from these isolates, have activity against this pest.

More specifically, the methods of the subject invention use B.t. microbes, or variants thereof, and/or their toxins, to control corn rootworms. Specific B.t. microbes useful according to the invention are B.t. PS80JJ1, B.t. PS158D5, B.t. PS167P, B.t. PS169E, B.t. PS177F1, B.t. PS177G, B.t. PS204G4, and B.t. PS204G6. Further, the subject invention also includes the use of variants of the exemplified B.t. isolates which have substantially the same corn rootworm-active properties as the specifically exemplified B.t. isolates. Such variants would include, for example, mutants. Procedures for making mutants are well known in the microbiological art. Ultraviolet light and nitrosoguanidine are used extensively toward this end.

The subject invention also includes the use of genes from the B.t. isolates of the invention which genes encode the corn rootworm-active toxins.

Still further, the invention includes the treatment of substantially intact B.t. cells, and recombinant cells containing the genes of the invention, treated to prolong the corn rootworm activity when the substantially intact cells are applied to the environment of a target pest. Such treatment can be by chemical or physical means, or a combination of chemical and physical means, so long as the chosen means do not deleteriously affect the properties of the pesticide, nor diminish the cell's capability of protecting the pesticide. The treated cell acts as a protective coating for the pesticidal toxin. The toxin becomes active upon ingestion by a target insect.

Finally, the subject invention concerns plants cells transformed with genes of the subject invention which encode corn rootworm-active toxins.

BRIEF DESCRIPTION OF THE SEQUENCES

SEQ ID NO. 1—is the N-terminal amino acid sequence for a toxin obtainable from PS204G6.

SEQ ID NO. 2—is an oligonucleotide probe used for cloning a gene from PS204G6.

SEQ ID NO. 3—is a forward primer used for PCR amplification of the 80J J1 and 167P genes.

SEQ ID NO. 4—is a reverse primer used for PCR amplification of the 80JJ1 and 167P genes.

SEQ ID NO. 5—is the nucleotide sequence of gene 80JJ1.

SEQ ID NO. 6—is the amino acid sequence of protein 80JJ1.

DETAILED DISCLOSURE OF THE INVENTION

Certain *Bacillus thuringiensis* stains useful according to the subject invention are disclosed in U.S. Pat. No. 5,151, 363. The disclosure of the cultures and their taxonomic characteristics are incorporated herein by reference to said patent.

The B.t. isolates of the subject invention have been deposited in the permanent collection of the Agricultural Research Service Patent Culture Collection (NRRL), Northern Regional Research Center, 1815 North University Street, Peoria, Ill. 61604, USA. The culture repository numbers of the B.t. strains are as follows:

| Culture | Repository No. | Deposit Date |
| --- | --- | --- |
| B.t. strain PS80JJ1 | NRRL B-18679 | July 17, 1990 |
| B.t. strain PS158D5 | NRRL B-18680 | July 17, 1990 |
| B.t. strain PS167P | NRRL B-18681 | July 17, 1990 |
| B.t. strain PS169E | NRRL B-18682 | July 17, 1990 |
| B.t. strain PS177F1 | NRRL B-18683 | July 17, 1990 |
| B.t. strain PS177G | NRRL B-18684 | July 17, 1990 |
| B.t. strain PS204G4 | NRRL B-18685 | July 17, 1990 |
| B.t. strain PS204G6 | NRRL B-18686 | July 17, 1990 |
| E. coli NM522 (pMYC2365) | NRRL- | |
| E. coli NM522 (pMYC2379) | NRRL B-21155 | Nov. 3, 1993 |

Certain of these culture deposits are now available to the public by virtue of the issuance of U.S. Pat. No. 5,151,363.

Other cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Genes and toxins. The genes and toxins useful according to the subject invention include not only the full length sequences disclosed but also fragments of these sequences, variants, mutants, and fusion proteins which retain the characteristic pesticidal activity of the toxins specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

It should be apparent to a person skilled in this art that genes encoding active toxins can be identified and obtained through several means. The specific genes exemplified herein may be obtained from the isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes which encode active fragments may be obtained using a variety of restriction enzymes. Proteases may be used to directly obtain active fragments of these toxins.

Equivalent toxins and/or genes encoding these equivalent toxins can be derived from B.t. isolates and/or DNA libraries using the teachings provided herein. There are a number of methods for obtaining the pesticidal toxins of the instant invention. For example, antibodies to the pesticidal toxins disclosed and claimed herein can be used to identify and isolate other toxins from a mixture of proteins. Specifically, antibodies may be raised to the portions of the toxins which are most constant and most distinct from other B.t. toxins. These antibodies can then be used to specifically identify equivalent toxins with the characteristic activity by immunoprecipitation, enzyme linked immunosorbent assay (ELISA), or western blotting. Antibodies to the toxins disclosed herein, or to equivalent toxins, or fragments of these toxins, can readily be prepared using standard procedures in this art. The genes which encode these toxins can then be obtained from the microorganism.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments retaining pesticidal activity are also included in this definition.

A further method for identifying the toxins and genes of the subject invention is through the use of oligonucleotide probes. These probes are detectable nucleotide sequences. These sequences may be detectable by virtue of an appropriate label or may be made inherently fluorescent as described in International Application No. WO93/16094. As is well known in the art, if the probe molecule and nucleic acid sample hybridize by forming a strong bond between the two molecules, it can be reasonably assumed that the probe and sample have substantial homology. Preferably, hybridization is conducted under stringent conditions by techniques well-known known in the art, as described, for example, in Keller, G. H., M. M. Manak (1987) *DNA Probes*, Stockton Press, New York, N.Y., pp. 169–170. Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using DNA synthesizer and standard procedures. These nucleotide sequences can also be used as PCR primers to amplify genes of the subject invention.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. This amino acid homology will typically be greater than 75%, preferably be greater than 90%, and most preferably be greater than 95%. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

The toxins of the subject invention can also be characterized in terms of the shape and location of toxin inclusions, which are described above.

Recombinant Hosts. The toxin-encoding genes harbored by the isolates of the subject invention can be introduced into a wide variety of microbial or plant hosts. Expression of the toxin gene results, directly or indirectly, in the intracellular production and maintenance of the pesticide. With suitable microbial hosts, e.g., Pseudomonas, the microbes can be applied to the situs of the pest, where they will proliferate and be ingested. The result is a control of the pest. Alternatively, the microbe hosting the toxin gene can be treated under conditions that prolong the activity of the toxin and stabilize the cell. The treated cell, which retains the toxic activity, then can be applied to the environment of the target pest.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurenti, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing a B.t. gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Treatment of cells. As mentioned above, B.t. or recombinant cells expressing a B.t. toxin can be treated to prolong the toxin activity and stabilize the cell. The pesticide microcapsule that is formed comprises the B.t. toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Hetty's fixative (See: Humason, Gretchen L., *Animal Tissue Techniques*, W. H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bio-availability or bioactivity of the toxin.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells of the invention can be cultured using standard art media and fermentation techniques. Upon completion of the fermentation cycle the bacteria can be harvested by first separating the B.t. spores and crystals from the fermentation broth by means well known in the art. The recovered B.t. spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations. Formulated bait granules containing an attractant and spores and crystals of the B.t. isolates, or recombinant microbes comprising the genes obtainable from the B.t. isolates disclosed herein, can be applied to the soil. Formulated product can also be applied as a seed-coating or root treatment or total plant treatment at later stages of the crop cycle. Plant and soil treatments of B.t. cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidaladditives, or surfactants. Liquid formulations may be aqueous-based or non-aqueous and employed as foams, gels, suspensions, emulsifiable concentrates, or the like. The ingredients may include theological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

Mutants. Mutants of the isolates of the invention can be made by procedures well known in the art. For example, an asporogenous mutant can be obtained through ethylmethane sulfonate (EMS) mutagenesis of an isolate. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous routants in shake flask media and selecting those mutants that are still intact and contain toxin crystals at the end of the fermentation. Lysis minus strains are suitable for a cell treatment process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phage lysate is placed in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

Example 1—Culturing of B.t. Isolates of the Invention

A subculture of the B.t. isolates, or mutants thereof, can be used to inoculate the following medium, a peptone, glucose, salts medium.

| Bacto Peptone | 7.5 g/l |
|---|---|
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| pH 7.2 | |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

Example 2—Purification of Protein and Amino Acid Sequencing

The *Bacillus thuringiensis* (B.t.) isolates were cultured as described in Example 1 or can be cultured using other standard media and fermentation techniques well-known in the art. Delta-endotoxins were isolated and purified by harvesting toxin protein inclusions by standard sedimentation centrifugation. Recovered parasporal inclusion bodies of some of the isolates were partially purified by sodium bromide (26–40%) isopycnic gradient centrifugation (Pfannenstiel, M. A., E. J. Ross, V. C. Kramer, K. W. Nickerson [1984] *FEMS Microbiol. Lett.* 21:39). Thereafter the individual toxin proteins were resolved by solubilizing the crystalline protein complex in alkali buffer and fractionating the individual proteins by DEAE-sepharose CL-6B (Sigma Chem. Co., St. Louis, Mo.) chromatography by step-wise increments of increasing concentrations of an NaCl-containing buffer (Reichenberg, D., in *Ion Exchangers in Organic and Biochemistry* [C. Calmon and T. R. E. Kressman, eds.], Interscience, New York, 1957).

Fractions containing a protein toxic to corn rootworm were bound to PVDF membrane (Millipore, Bedford, Mass,) by western blotting techniques (Towbin, H., T. Staehelin, K. Gordon [1979] *Proc. Natl. Acad. Sci. USA* 76:4350) and the N-terminal amino acids determined by the standard Edman reaction with an automated gasphase sequenator (Hunkapiller, M. W., R. M. Hewick, W. L. Dreyer, L. E. Hood [1983] *Meth. Enzymol.* 91:399).

The sequence obtained from the PS204G6 20–25 kDa polypeptide was:

G N F N X E K D Y D (SEQ ID NO. 1)

where X represents an amino acid residue with an undetermined identity. From this sequence data oligonucleotide probes were designed by utilizing a codon frequency table assembled from available sequence data of other B.t. toxin genes. The probes can be synthesized on an Applied Biosystems, Inc. DNA synthesis machine.

Example 3—Molecular Cloning and Expression of Gene Encoding a Toxin from *Bacillus thudngiensis* Strain PS204G6

Total cellular DNA was prepared from Bacillus thuringiensis (B.t.) cells grown to an optical density, at 600 nm, of 1.0. Cells were pelleted by centrifugation and resuspended in protoplast buffer (20 mg/ml lysozyme in 0.3M sucrose, 25 mM Tris-Cl (pH 8.0), 25 mM EDTA). After incubation at 37° C. for 1 hour, protoplasts were lysed by two cycles of freezing and thawing. Nine volumes of a solution of 0.1M NaCl, 0.1% SDS, 0.1M Tris-Cl were added to complete lysis. The cleared lystate was extracted twice with phenol:chloroform (1:1). Nucleic acids were precipitated with two volumes of ethanol and pelleted by centrifugation. The pellet was resuspended in TE buffer and RNase was added to a final concentration of 50/µg/ml. After incubation at 37° C. for 1 hour, the solution was extracted once each with phenol:chloroform (1:1) and TE-saturated chloroform. DNA was precipitated from the aqueous phase by the addition of one-tenth volume of 3M NaOAc and two volumes of ethanol. DNA was pelleted by centrifugation, washed with 70% ethanol, dried, and resuspended in TE buffer.

An oligonucleotide probe with the following sequence was synthesized based on the PS204G6 20–25 kDa toxin peptide sequence:

5' AGACGTGGATCCGGAAATTTTAATTTT
GAAAA(AG)GA(CT)TA(CT)GA 3'
(SEQ ID NO. 2)

This oligonucleotide contains a 5' BamHI cloning site and is mixed at three positions as shown. This probe was radiolabeled with $^{32}P$ and used in standard hybridizations of Southern blots of PS204G6 total cellular DNA. Hybridizing bands included an approximately 2.4 kbp HindIII fragment. This DNA fragment contains all or a fragment of this PS204G6 toxin gene.

A gene library was constructed from PS204G6 DNA partially digested with Sau3A. Partial restriction digests were fractionated by agarose gel electrophoresis. DNA fragments 9.3 to 23 kbp in size were excised from the gel, electroeluted from the gel slice, purified on an Elutip-D ion exchange column (Schleicher and Schuell, Keene, N.H.), and recovered by ethanol precipitation. The Sau3A inserts were ligated into BamHI-digested LambdaGem-11 (Promega, Madison, Wis.). Recombinant phage were packaged and plated on *E. coli* KW251 cells. Plaques were screened by hybridization with the radiolabeled probe described above. Hybridizing phage were plaque-purified and used to infect liquid cultures of *E. coli* KW251 cells for isolation of DNA by standard procedures (Maniatis et al, supra.).

For subcloning the gene encoding the PS204G6 toxin, preparative amounts of phage DNA were digested with EcoRI+SalI and electrophoresed on an agrose gel. The approximately 5.5 kbp band containing the toxin gene was excised from the gel, electroeluted from the gel slice, and purified by ion exchange chromatography as described above. The purified DNA insert was ligated into EcoRI+ Sal1-digested pHTBlueII (an *E. coli/B. thuringiensis* shuttle vector comprised of pBluescript S/K (Stratagene, La Jolla, Calif.) and the replication origin from a resident B.t. plasmid [D. Lereclus et al. (1989) *FEMS Microbiology Letters* 60:211–218]). The ligation mix was used to transform frozen, competent *E. coli* NM522 cells (ATCC 47000). β-galactosidase⁻ transformants were screened by restriction digestion of alkaline lysate plasmid minipreps. The desired plasmid construct, pMYC2365, contains a toxin gene that is novel compared to other δ-endotoxin genes.

pMYC2365 was introduced into the acrystalliferous (Cry⁻) B.t. host, CryB (A, Aronson, Purdue University, West Lafayette, Ind.), by electroporation. Expression of an approximately 75–85 kDa toxin was demonstrated by SDS-PAGE analysis. The polypeptide profile of the cloned toxin was similar to that of purified native PS204G6 crystals. In addition to the 75–85 kDa polypeptide, both native and cloned toxins exhibited the approximately 20–25 kDA polypeptide.

Example 4—Cloning and Expression of a Novel Toxin Gene from *Bacillus thudngiensis* strain PS80JJ1

Total cellular DNA was prepared from B.t. cells as described in Example 3. An approximately 700–800 bp DNA fragment from a novel PS80JJ1 130 kDa toxin gene was obtained by polymerase chain reaction (PCR) amplification using PS80JJ1 cellular DNA and the following primers:

"Forward":
5' GGACCAGGATTTACAGG(TA)GG(AG)(AG)A 3'
(SEQ ID NO. 3)

"Reverse":
5' TAACGTGTAT(AT)CG(CG)TTTTAATTT(TA)GA(CT)TC 3'
(SEQ ID NO. 4).

The DNA fragment was cloned into pBluescript S/K (Stratagene, LaJolla, Calif.) and partially sequenced by dideoxynucleotide DNA sequencing methodology (Sanger et al. [1977] *Proc. Natl. Acad. Sci. USA* 74:5463–5467) using Sequenase (US Biochemicals, Cleveland, Ohio). DNA sequences unique to at least one PS80JJ1 toxin gene were identified by computer comparison with other known δ-endotoxin genes.

The 700–800 bp DNA fragment was radiolabelled with $^{32}$P and used in standard hybridizations of Southern blots of PS80JJ1 total cellular DNA. Hybridizing bands included an approximately 1.8 kbp EcoRI fragment and an approximately 9.5 kbp HindIII fragment. These hybridizing DNA bands contain toxin genes or restriction fragments of toxin genes from PS80JJ1.

A gene library was constructed from PS80JJ1 DNA partially digested with NdeII. Partial restriction digests were fractionated by agarose gel electrophoresis. DNA fragments 93 to 23 kbp in size were excised from the gel, electroeluted from the gel slice, purified on an Elutip-D ion exchange column (Schleicher and Schuell, Keene, N.H.), and recovered by ethanol precipitation. The NdeII inserts were ligated into BamHI-digested LambdaGem-11 (Promega, Madison, Wis.). Recombinant phage were packaged and plated on *E. coil* KW251 cells. Plaques were screened by hybridization with the probe described above. Hybridizing phage were plaque-purified and used to infect liquid cultures of *E. coli* KW251 cells for isolation of DNA by standard procedures (Maniatis et al., supra).

For subcloning the gene encoding the PS80JJ1 130 kDa toxin, preparative amounts of phage DNA were digested with XhoI and electrophoresed on an agarose gel. The approximately 12 kbp band containing the toxin gene was excised from the gel, electroeluted from the gel slice, and purified by ion exchange chromatography as described above. The purified DNA insert was ligated into XhoI-digested pHTBlueII (an *E. coli/B. thuringiensis* shuttle vector comprised of pBluescript S/K [Stratagene, La Jolla, Calif.] and the replication origin from a resident B.t. plasmid [D. Lereclus et al. [1989] *FEMS Microbiology Letters* 60:211–218]). The ligation mix was used to transform frozen, competent *E. coli* NM522 cells (ATCC 47000). β-galactosidase-transformants were screened by restriction digestion of alkaline lysate plasmid minipreps as above. The desired plasmid construct, pMYC2379, contains a toxin gene that is novel compared to other toxin genes containing insecticidal proteins.

Sequence analysis of the toxin gene revealed that it encodes a protein of approximately 130,000 daltons, deduced from the DNA sequence. The nucleotide and deduced amino acid sequences are shown in SEQ ID NOS. 5 and 6, respectively.

pMYC2379 was introduced into the acrystalliferous (Cry⁻) B.t. host, CryB (A. Aronson, Purdue University, West Lafayette, Ind.), by electroporation. Expression of the 130kDa toxin was demonstrated by SDS-PAGE analysis.

The PS80JJ1 toxin gene encoded by pMYC2379 was sequenced using the ABI373 automated sequencing system and associated software.

Example 5—Restriction Fragment Length Polymorphism Analysis of δ-endotoxin Genes From *Bacillus thuringiensis* strain PS167P Total cellular DNA was prepared from *Bacillus thuringiensis* (B.t.) cells as described in Example 3.

An approximately 700–800 bp DNA fragment from novel PS167P 130 kDa toxin genes was obtained by polymerase chain reaction (PCR) amplification using PS167P cellular DNA and the primers shown in SEQ ID NO. 3 and SEQ ID NO. 4. This DNA fragment was cloned into pBluescript S/K (Stratagene, LaJolla, Calif.) and partially sequenced by dideoxynucleotide DNA sequencing methodology (Sanger et al, supra) using Sequenase (US Biochemicals, Cleveland, Ohio). DNA sequences unique to at least two PS167P toxin genes were identified by computer comparison with other known δ-endotoxin genes.

The 700–800 bp DNA fragment was radiolabeled with $^{32}$P and used in standard hybridizations of Southern blots of PS167P total cellular DNA. Hybridizing bands included approximately 1.8 kbp and 2.3 kbp EcoRI fragments and approximately 5.5 kbp and 8.0 kbp HindIII fragments. These DNA fragments contain toxin genes or restriction fragments of toxin genes unique to PS167P.

Example 6—Insertion of Toxin Genes Into Plants

One aspect of the subject invention is the transformation of plants with genes encoding the insecticidal toxin. The transformed plants are resistant to attack by the target pest.

Genes encoding pesticidal toxins, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUG series, M13mp series, pACYC184, etc. Accordingly, the sequence encoding the B.t. toxin can be inserted into the vector at a suitable restriction site. The resulting plasmid is used for transformation into *E. coli*. The *E. coli* cells are cultivated in a suitable nutrient medium, then harvested and lysed. The plasmid is recovered.

Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 120 516; Hoekema (1985) In: *The Binary Plant Vector System*, Offset-durkkerij Kanters B. V., Alblasserdam, Chapter 5; Fraley et al., Crit. Rev. Plant Sci. 4:1–46; and An et al. (1985) EMBO J. 4:277–287.

Once the inserted DNA has been integrated in the genome, it is relatively stable there and, as a rule, does not come out again. It normally contains a selection marker that coffers on the transformed plant cells resistance to a biocide or an antibiotic, such as kanamycin, G 418, bleomyein, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al. [1978] *Mol. Gen. Genet.* 163:181–187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. Also, advantageously, plants encoding a truncated toxin will be used. The truncated toxin typically will encode about 55% to about 80% of the full length toxin. Methods for creating synthetic B.t. genes for use in plants are known in the art.

Example 7—Cloning of B.t. Genes Into Insect Viruses

A number of viruses are known to infect insects. These viruses include, for example, baculoviruses and entomopoxviruses. In one embodiment of the subject invention, genes encoding the insecticidal toxins, as described herein, can be placed within the genome of the insect virus, thus enhancing the pathogenicity of the virus. Methods for constructing insect viruses which comprise B.t. toxin genes are well known and readily practiced by those skilled in the art. These procedures are described, for example, in Merryweather et al. (Merryweather, A. T., U. Weyer, M. P. G. Harris, M. Hirst, T. Booth, R. D. Possee (1990) *J. Gen. Virol.* 7/:1535–1544) and Martens et al. (Martens, J. W. M., G. Honee, D. Zuidema, J. W. M. van Lent, B. Visser, J. M. Vlak (1990) *Appl. Environmental Microbid.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for controlling corn rootworms comprising contacting said corn rootworms with a corn rootworm-controlling amount of a *Bacillus thuringiensis* isolate, or a toxin of said *Bacillus thuringiensis* isolate, wherein said isolate is selected from the group consisting of PS80JJ1, having the identifying characteristics of NRRL B-18679; PS158D5, having the identifying characteristics of NRRL B-18680; PS167P, having the identifying characteristics of NRRL B-18681; PS169E, having the identifying characteristics of NRRL B-18682; PS177F1, having the identifying characteristics of NRRL B-18683; PS177G, having the identifying characteristics of NRRL B-18684; PS204G4, having the identifying characteristics of NRRL B-18685; and PS204G6, having the identifying characteristics of NRRL B-18686; and mutants thereof which retain activity against corn rootworms.

2. A method, according to claim 1, further comprising incorporating said *Bacillus thuringiensis* isolate, or a spore or toxin from said isolate, into a bait granule and placing said granule on or in the soil when planting corn or later in the crop cycle.

3. The method, according to claim 1, wherein said *Bacillus thuringiensis* isolate is PS80JJ1, having the identifying characteristics of NRRL B-18679.

4. The method, according to claim 1, wherein said *Bacillus thuringiensis* isolate is PS158D5, having the identifying characteristics of NRRL B-18680.

5. The method, according to claim 1, wherein said *Bacillus thuringiensis* isolate is PS167P, having the identifying characteristics of NRRL B-18681.

6. The method, according to claim 1, wherein said *Bacillus thuringiensis* isolate is PS169E, having the identifying characteristics of NRRL B-18682.

7. The method, according to claim 1, wherein said *Bacillus thuringiensis* isolate is PS177F1, having the identifying characteristics of NRRL B-18683.

8. The method, according to claim 1, wherein said *Bacillus thuringiensis* isolate is PS177G, having the identifying characteristics of NRRL B-18684.

9. The method, according to claim 1, wherein said *Bacillus thuringiensis* isolate is PS204G4, having the identifying characteristics of NRRL B-18685.

10. The method, according to claim 1, wherein said *Bacillus thuringiensis* isolate is PS204G6, having the identifying characteristics of NRRL B-18686.

11. A method for controlling corn rootworms comprising contacting said corn rootworms with a corn rootworm-controlling effective amount of a pesticidal composition comprising substantially intact treated cells having prolonged pesticidal activity when applied to the environment of the corn rootworm, wherein said insecticide is produced by a *Bacillus thuringiensis* gene from a *Bacillus thuringiensis* isolate selected from the group consisting of PS80JJ1, having the identifying characteristics of NRRL B-18679; PS158D5, having the identifying characteristics of NRRL B-18680; PS167P, having the identifying characteristics of NRRL B-18681; PS169E, having the identifying characteristics of NRRL B-18682; PS177F1, having the identifying characteristics of NRRL B-18683; PS177G, having the identifying characteristics of NRRL B-18684; PS204G4, having the identifying characteristics of NRRL B-18685; and PS204G6, having the identifying characteristics of NRRL B-18686; and mutants thereof which retain activity against corn rootworms.

* * * * *

UNITED STATES PATENT AND TRADEMARK OFFICE
CERTIFICATE OF CORRECTION

PATENT NO. : 5,632,987  
DATED : May 27, 1997  
INVENTOR(S) : Jewel Payne, Kenneth E. Narva Page 1 of 3

It is certified that error appears in the above-identified patent and that said Letters Patent is hereby corrected as shown below:

Column 1, lines 48&49: "*Use of Entomogenous Bacteria in Agroecosystems,*" should read --Use of Entomogenous Bacteria in Agroecosystems,--(should not be italicized)

line 55: "*Agetastica alni.*" should read --*Agelastica alni.*--

Column 2, lines 11&12: "*Bacillus thudngiensis*" should read --*Bacillus thuringiensis*--

Column 3, line 21: "80J J1" should read --80JJ1-- line 53:

| Culture | Repository No. | Deposit Date |
|---|---|---|
| *E. coli* NM522 (pMYC2365) | NRRL- | | should read:

| Culture | Repository No. | Deposit Date |
|---|---|---|
| *E. coli* NM522 (pMYC2365) | NRRL-B-21155 | Nov. 3, 1993 |

UNITED STATES PATENT AND TRADEMARK OFFICE
CERTIFICATE OF CORRECTION

PATENT NO. : 5,632,987
DATED : May 27, 1997
INVENTOR(S) : Jewel Payne, Kenneth E. Narva It is certified that error appears in the above-identified patent and that said Letters Patent is hereby corrected as shown below:

Column 4, line 24: "Bal31" should read --Bal31--

Column 6, line 38: "*C. diffiuens, C. laurenti*" should read --*C. diffluens, C. laurentii*--

Column 7, line 15: "Hetty's fixative" should read --Helly's fixative--

Column 8, line 17: "theological" should read --rheological-- line 43: "routants" should read --mutants--

Column 9, line 61: "(Millipore, Bedford, Mass.)" should read --(Millipore, Bedford, MA)-- line 67: "Enzymol 91:399)." should read --*Enzymol*. 91:399).

Column 10, line 13: "*thudngiensis*" should read --*thuringiensis*-- line 26: "50/ug/ml." should read --50 ug/ml.--

Column 11, line 23: "*thudngiensis*" should read --*thuringiensis*-- line 55: "93 to 23 kbp" should read --9.3 to 23 kbp--

UNITED STATES PATENT AND TRADEMARK OFFICE
CERTIFICATE OF CORRECTION

PATENT NO. : 5,632,987

DATED : May 27, 1997

INVENTOR(S) : Jewel Payne, Kenneth E. Narva

It is certified that error appears in the above-identified patent and that said Letters Patent is hereby corrected as shown below:

Column 12, line 62: "pUG Series," should read --pUC Series,--

Column 13, line 10: "fight border," should read --right border,-- line 23: "bleomyein," should read --bleomycin,--

Column 14, line 42: "7/:1535-1544)" should read --71:1535-1544)-- line 44: "*Microbid.*" should read --*Microbiol.*--

Signed and Sealed this

Second Day of December, 1997

*Attest:*

BRUCE LEHMAN

*Attesting Officer*      *Commissioner of Patents and Trademarks*